United States Patent
Hahn et al.

(10) Patent No.: US 9,937,353 B2
(45) Date of Patent: Apr. 10, 2018

(54) SYSTEMS AND METHODS FOR INCREASING STIMULATION DOSE

(75) Inventors: Stephen J. Hahn, Shoreview, MN (US); Jason J. Hamann, Blaine, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1691 days.

(21) Appl. No.: 13/306,745

(22) Filed: Nov. 29, 2011

(65) Prior Publication Data

US 2012/0143286 A1   Jun. 7, 2012

Related U.S. Application Data

(60) Provisional application No. 61/420,567, filed on Dec. 7, 2010.

(51) Int. Cl.
*A61N 1/372* (2006.01)
*A61N 1/36* (2006.01)
*A61N 1/05* (2006.01)

(52) U.S. Cl.
CPC ....... *A61N 1/37282* (2013.01); *A61N 1/3615* (2013.01); *A61N 1/36132* (2013.01); *A61N 1/36178* (2013.01); *A61N 1/36185* (2013.01); *A61N 1/37252* (2013.01); *A61N 1/0556* (2013.01)

(58) Field of Classification Search
None
See application file for complete search history.

(56) References Cited

U.S. PATENT DOCUMENTS

| 5,928,272 | A | 7/1999 | Adkins et al. |
| 6,477,404 | B1 | 11/2002 | Yonce et al. |
| 8,600,505 | B2 | 12/2013 | Libbus et al. |
| 2005/0065575 | A1 | 3/2005 | Dobak |
| 2005/0075702 | A1* | 4/2005 | Shafer ............. 607/72 |

(Continued)

FOREIGN PATENT DOCUMENTS

| CN | 103249453 A | 8/2013 |
| JP | 2003511163 A | 3/2003 |

(Continued)

OTHER PUBLICATIONS

Arcot-Krishnamurthy, Shantha, et al., "Systems and Methods to Account for Neck Movement During Nerve Stimulation", U.S. Appl. No. 61/478,688, filed Apr. 25, 2011, 56 pgs.

(Continued)

*Primary Examiner* — Erica Lee
(74) *Attorney, Agent, or Firm* — Schwegman Lundberg & Woessner, P.A.

(57) ABSTRACT

According to an embodiment of a method performed by an implantable medical device to deliver a neural stimulation therapy to a patient, a lower dose of the neural stimulation therapy is delivered to the patient. The dose of the neural stimulation therapy is automatically increased from the lower dose to a higher dose, and the higher dose of the neural stimulation therapy is delivered to the patient. A trigger that is controlled by the patient is detected, and the dose of the neural stimulation therapy is automatically returned from the higher dose back to the lower dose in response to detecting the trigger.

15 Claims, 10 Drawing Sheets

(56) References Cited

U.S. PATENT DOCUMENTS

| | | |
|---|---|---|
| 2007/0142864 A1* | 6/2007 | Libbus et al. ............... 607/2 |
| 2008/0058871 A1 | 3/2008 | Libbus et al. |
| 2008/0140000 A1 | 6/2008 | Shuros et al. |
| 2008/0243196 A1 | 10/2008 | Libbus et al. |
| 2010/0010556 A1 | 1/2010 | Zhao et al. |
| 2010/0168820 A1* | 7/2010 | Maniak et al. ............ 607/63 |
| 2010/0228310 A1* | 9/2010 | Shuros et al. ............. 607/17 |
| 2010/0274320 A1* | 10/2010 | Torgerson ................. 607/59 |
| 2011/0015702 A1 | 1/2011 | Ternes et al. |
| 2011/0015703 A1 | 1/2011 | Ternes et al. |
| 2011/0015704 A1 | 1/2011 | Ternes et al. |
| 2011/0282416 A1 | 11/2011 | Hamann et al. |

FOREIGN PATENT DOCUMENTS

| | | |
|---|---|---|
| JP | 2015500098 A | 1/2014 |
| WO | WO-2010123704 A2 | 10/2010 |

OTHER PUBLICATIONS

Chavan, Abhi V, et al., "Method and Apparatus for Controlling Neurostimulation According to Physical State", U.S. Appl. No. 13/272,786, filed Oct. 13, 2011, 79 pgs.

Hahn, Stephen J, et al., "Systems and Methods for Increasing Stimulation Dose", U.S. Appl. No. 61/420,567, filed Dec. 7, 2010, 40 pgs.

Ordonez, Juan Gabriel Hincapie, et al., "Automatic Neural Stimulation Titration Sweep", U.S. Appl. No. 13/155,549, filed Jun. 8, 2011, 37 pgs.

Ordonez, Juan Gabriel Hincapie, et al., "Systems & Methods to Detect Vagus Capture", U.S. Appl. No. 61/526,568, filed Aug. 23, 2011, 68 pgs.

"Chinese Application Serial No. 201180058945.3, Office Action dated Jun. 19, 2014", With English Translation, 17 pgs.

"Chinese Application Serial No. 201180058945.3, Office Action dated Nov. 18, 2014", 16 pgs.

"International Application Serial No. PCT/US2011/062451, International Preliminary Report on Patentability dated Jun. 20, 2013", 7 pgs.

"International Application Serial No. PCT/US2011/062451, Search Report dated May 10, 2012", 3 pgs.

"International Application Serial No. PCT/US2011/062451, Written Opinion dated May 10, 2012", 6 pgs.

"Japanese Application Serial No. 2013-543210, Office Action dated Jun. 11, 2014", With English Translation, 7 pgs.

* cited by examiner

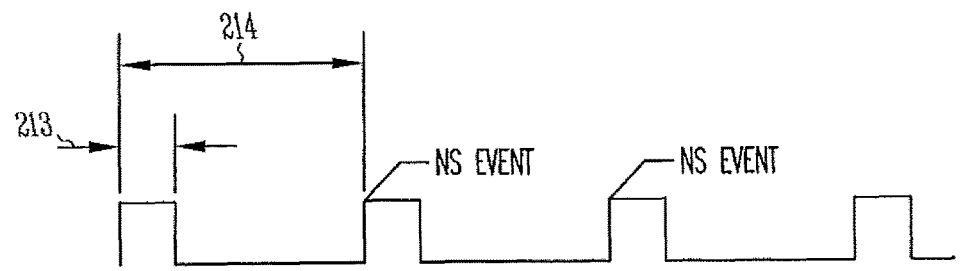
Fig.2
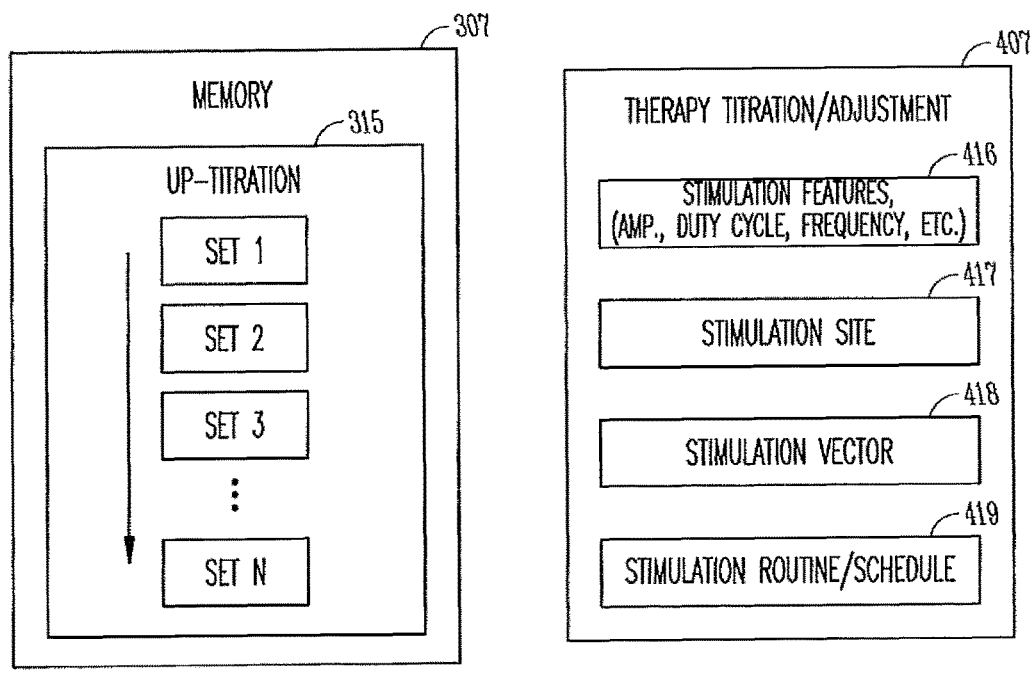
Fig.3
Fig.4

SYSTEMS AND METHODS FOR INCREASING STIMULATION DOSE

CLAIM OF PRIORITY

This application claims the benefit of priority under 35 U.S.C. § 119(e) of Hahn et al., U.S. Provisional Patent Application Ser. No. 61/420,567, entitled SYSTEMS AND METHODS FOR INCREASING STIMULATION DOSE", filed on Dec. 7, 2010, which is herein incorporated by reference in its entirety.

TECHNICAL FIELD

This application relates generally to medical devices and, more particularly, to systems, devices and methods for setting a dose of a neural stimulation therapy.

BACKGROUND

Implantable Medical Devices (IMDs) have been designed or proposed to treat various conditions. For example, some IMDs are designed to treat cardiac conditions and perform functions such as pacing, cardioversion and defibrillation. Some IMDs deliver neural stimulation. By way of example and not limitation, neural stimulation has been proposed as a therapy for respiratory problems such a sleep disordered breathing, blood pressure control such as to treat hypertension, cardiac rhythm management, myocardial infarction and ischemia, heart failure, epilepsy, depression, pain, migraines, eating disorders, obesity, inflammatory diseases, and movement disorders. NeuroCardiac Therapy (NCT), as used herein, refers to neural stimulation delivered for a cardiovascular therapy. NCT, by way of example and not limitation, includes the stimulation of an autonomic neural target to provide a therapy for a cardiac arrhythmia, ischemia, heart failure, angina, atherosclerosis, blood pressure, and the like. By way of example and not limitation, autonomic neural targets used to deliver NCT include the vagus nerve, cardiac branches of the vagal nerves, baroreceptors, chemoreceptors, cardiac fat pads, the spinal column or some nerve roots extending from the spinal column.

SUMMARY

An embodiment of an implantable neural stimulator for implantation in a patient comprises controller circuitry, neural stimulation output circuitry, an input, and a memory. The neural stimulation output circuitry is configured to deliver neural stimulation, and the controller circuitry is configured to control an intensity of the neural stimulation delivered by the neural stimulation output circuitry. The input is configured to receive a trigger from the patient, wherein the controller circuitry is configured to detect the trigger. The controller circuitry operates on instructions in the memory. The instructions include instructions for delivering neural stimulation using the neural stimulation output circuitry, instructions for implementing an up-titration routine to automatically increase the intensity of the neural stimulation from a lower intensity level to a higher intensity level, and instructions for automatically decreasing the intensity of the neural stimulation from the higher intensity level to the lower intensity level in response to receiving the trigger from the patient. The automatically increased intensity is maintained if the trigger from the patient is not received.

According to an embodiment of a method performed by an implantable medical device to deliver a neural stimulation therapy to a patient, a lower dose of the neural stimulation therapy is delivered to the patient, the dose of the neural stimulation therapy is automatically increased from the lower dose to a higher dose, and the higher dose of the neural stimulation therapy is delivered to the patient unless a patient-controlled trigger is detected. If a trigger controlled by the patient is detected, the dose of the neural stimulation therapy is automatically returned from the higher dose back to the lower dose.

A system embodiment for delivering a neural stimulation therapy to a patient comprises means for delivering a lower dose of the neural stimulation therapy to the patient, means for automatically increasing the dose of the neural stimulation therapy from the lower dose to a higher dose, and delivering the higher dose of the neural stimulation therapy to the patient, means for detecting a trigger that is controlled by the patient, and means for automatically returning the dose of the neural stimulation therapy from the higher dose back to the lower dose in response to detecting the trigger.

According to an embodiment performed by an implantable medical device, a neural stimulation therapy is delivered to the patient, and a programmed routine is used to intermittently and incrementally increase a dose of the neural stimulation therapy to increase the dose by a plurality of dose increments over time. The programmed routine is used to deliver the neural stimulation using the increased dose after each of the plurality of dose increments, monitor for a patient-controlled request to reduce the dose, and respond to the patient-controlled request by reducing the dose by at least one of the plurality of dose increments.

A system embodiment comprises a neural stimulator and a controller. The neural stimulator is configured to deliver neural stimulation therapy to the patient. The controller is configured to perform a programmed routine to intermittently and incrementally increase a dose of the neural stimulation therapy to increase the dose by a plurality of dose increments over time, deliver the neural stimulation using the increased dose after each of the plurality of dose increments, monitor for a patient-controlled request to reduce the dose, and respond to the patient-controlled request by reducing the dose by at least one of the plurality of dose increments.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 2 illustrates a representation of intermittent neural stimulation (INS).

FIG. 3 illustrates a memory, according to various embodiments, that includes instructions, operable on by the stimulation control circuitry, for controlling an up-titration routine by progressively stepping up through defined parameter sets (e.g. parameter set 1 through parameter set N), where each set incrementally increases the stimulation dose or intensity of the stimulation therapy.

FIG. 4 illustrates an embodiment of a therapy titration module such as is illustrated in FIG. 1.

DETAILED DESCRIPTION

Figure 1:
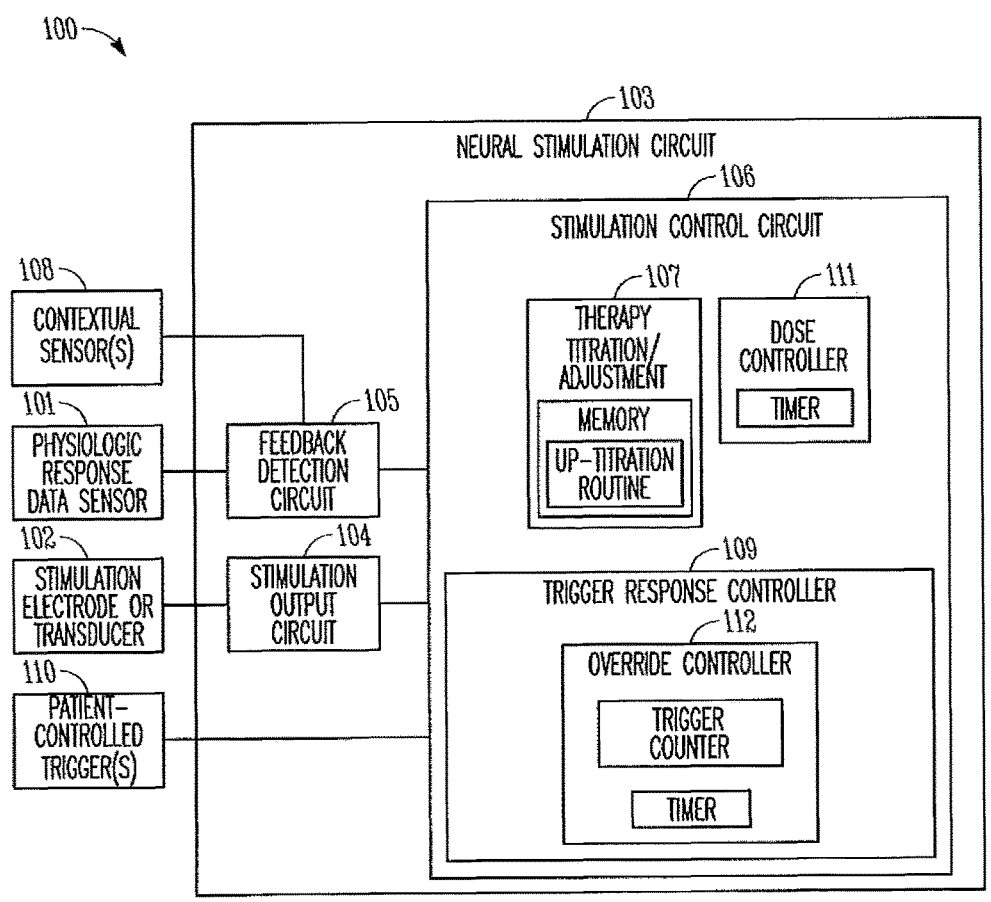
FIG. 1 is a block diagram illustrating an embodiment of a neural stimulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Some current and proposed neural stimulation therapies are delivered for periods on the order of minutes, days, weeks, months or years. If the neural stimulation therapy is associated with an undesired response, the chronic nature of the therapy may exacerbate the undesirability of the response, as it can have long-term consequences for the health or quality of life for the patient. By way of example and not limitation, the therapy may change heart rate and blood pressure at undesirable times, or may cause laryngeal vibration or cough attributed to vagal nerve stimulation. An undesirable response to the therapy may affect the patient's compliance with the therapy. For example, if the patient has the ability to turn off the therapy to avoid the undesired response, the patient may choose to leave the therapy off. If the patient has no control over the therapy, then the patient may not agree to the treatment at all if the patient is concerned about the undesired response.

Various embodiments of the present subject matter provide an implanted medical device configured to provide a device-based up-titration routine to automatically increase the neural stimulation dose according to a programmed schedule, with a patient-activated back-out that allows the patient to override or reverse the last increment. Some studies suggest that the ability to up-titrate the dose of a neural stimulation therapy, such as NCT, is important for both patient tolerability and therapeutic efficacy. It is currently believed that patients gradually accommodate to neural stimulation therapy, and that higher neural stimulation levels equate to improved efficacy. Thus, it is believed that it may be desirable to deliver a dose of neural stimulation sufficiently large to be efficacious, but it may be desirable to achieve the desired dose by stepping through progressively increasing doses of neural stimulation where the dose increments are sufficiently small to encourage patient tolerability. Manual titration via multiple clinic visits is unlikely to have broad acceptance and therefore limit adoption. Device-based auto-up-titration alone may not assure patient tolerability because of technical challenges in automatically detecting symptoms of patient tolerability. Furthermore, patient-based titration alone may not assure maximal dosage, as patients may not be motivated to up-titrate on their own.

Some embodiments of the present subject matter are configured to deliver open loop stimulation, wherein the device is configured to provide an automatic up-titration routine with a patient activated back-out. Some embodiments of the present subject matter are configured to deliver close loop stimulation wherein the device is configured to provide an automatic up-titration routine with a patient activated back-out using sensed physiological feedback to control the up-titration routine.

FIG. 1 is a block diagram illustrating an embodiment of a neural stimulation system 100. The system 100 includes a data sensor 101 adapted to sense a physiologic parameter, a stimulation electrode/transducer 102, and a neural stimulation circuit 103. The neural stimulation circuit 103 includes a stimulation output circuit 104, a feedback detection circuit 105, and a stimulation control circuit 106. The stimulation control circuit 106 controls the delivery of the neural stimulation pulses and includes a therapy titration adjustment circuit or module 107. The stimulation output circuit 104 delivers the neural stimulation pulses upon receiving a pulse delivery signal from stimulation control circuit 106. The data sensor 101 provides signals indicative of a physiological response to the applied neural stimulation. A feedback detection circuit 105 receives the signal indicative of the response and processes the signal to provide a neural stimulation feedback signal. In various embodiments, the response includes a cardiac activity such as heart rate, HRV, HRT, PR interval, T-wave velocity, or action potential duration. In various embodiments the response includes a non-cardiac response such as respiration or blood pressure. In various embodiments, the response includes a QT interval or atrial/ventricular refractory periods. In some embodiments, the therapy titration/adjustment module 107 uses the feedback signal to modulate or titrate the therapy generated by the stimulation output circuit 104 to provide the desired physiologic response (e.g. cardiac response or non-cardiac response). Some embodiments include contextual sensor(s) or input(s) 108 connected to the feedback detection circuit 105 to provide a more complete picture of a patient's physiology. The feedback detection circuit can provide the neural stimulation feedback signal based on the physiological response data sensor(s) 101 and the contextual input(s) 108. The contextual input(s) can be used to avoid incomplete data from affecting the neural stimulation. Examples of contextual inputs include an activity sensor, a posture sensor and a timer. Another example of a contextual input is an input that is indicative of a patient's environment (e.g. in bedroom or car). Any one or combination of two or more contextual inputs can be used by the feedback detection circuit. For example, an elevated heart rate may be representative of exercise rather than a reason for titrating the neural stimulation therapy.

The illustrated stimulation control circuit 106 includes a trigger response controller 109, which is configured to respond to a patient-controlled trigger 110. The system may be configured to use a patient-friendly back-out activator, such as a magnet, a handheld programmer, Latitude-style communicator, a hand tap on the body near the implanted device, a hand-held vibrating device with a defined mechanical vibration frequency similar to the vibration of a toothbrush, a hand-held device that uses sound at a set frequency, a hand-held device that emits a light (e.g. red or near infrared) pulsing at a set frequency, and the like. According to various embodiments, the system is configured to allow the ambulatory patient to back out the last increment, or the last two or more increments. It may be reasonably assumed that a previous increment value was tolerable by the patient and the backing out to that previous value will be acceptable by the patient. Therefore, some embodiments only allow the patient to back out one increment.

Some system embodiments are configured to allow a physician to program the number of increments that are allowed to be backed out by the patient. Some embodiments allow the patient to back out more than one increment. If the patient has backed out to a previous increment, the system will attempt to increase the dose again at the next scheduled increment. After a defined number of patient back-out requests, the system stops attempting to increase the dose. The defined number of patient back-out requests may be programmable by the physician, according to various embodiments. Some system embodiments are configured to automatically change the frequency of scheduled increments after a defined number of patient back-out requests. For example, the system may only titrate monthly rather than weekly to allow the patient more time to adjust to the higher dose of neural stimulation. Some system embodiments are configured to change the amount or size of the increment for the next scheduled increment after a defined number of patient back-out requests. Various combinations of these may be used after a defined number of patient back-out requests.

According to various embodiments, the increment size is determined based on the current intensity level. By way of example and not limitation, an embodiment may determine the increment to be 0.3 mA if the current level is less than 1.5 mA, 0.2 mA if between 1.5 mA and 2.5 mA, and 0.1 mA if greater than 2.5 mA. In some embodiments, the increment size is determined based on whether the patient has previously requested a back-out. By way of example and not limitation, an embodiment determines the increment to be 0.3 mA until a patient requests a back-out, and then 0.1 mA after the patient requests a back-out. These embodiments use current amplitude as a measure of an intensity level. Intensity levels may be determined by other signal parameters, or sets of parameters, such as frequency, duty cycle, duration, and burst interval as discussed with respect to FIG. 1. Additionally or alternatively, an intensity level for neural stimulation may be determined by a distance to a neural stimulation target, and such may be adjusted using different sets of electrodes to provide different stimulation vectors to the neural stimulation target.

Some embodiments do not allow a patient to back off until a set or a physician-programmable period of time (e.g. minutes or hours) has passed at the new stimulation intensity level. Some embodiments require a patient to confirm that the stimulation is acceptable after an auto-up titration, and will back off after a set or physician programmable period of time if a confirmation is not received. Some embodiments up-increment for a short period of time, will back off if the patient does not confirm that the stimulation dose is acceptable, but will not back off after several attempts if the patient neither provides a confirmation that the stimulation dose is acceptable nor provides a patient-command that the stimulation dose is not acceptable.

Various device embodiments log or track up-increments and patient-requested back-outs in memory. This data can be used to generate a report at clinic visits. Some system embodiments generate alerts (e.g. Latitude-style) to notify a doctor if a patient is requesting too many back-outs. Some embodiments monitor the time interval between the up-titration and the patient-requested back-out. If the time interval is relatively consistent and relatively long (e.g. hours rather than minutes), some system embodiments up-titrate the therapy for a limited time consistent with the amount of time that the patient has been able to tolerate the increased intensity. Some embodiments log the time of a patient back-out. If the time of the time of the patient back-out is relatively consistent corresponding to a particular time of day (e.g. morning or evening), some embodiments automatically create a schedule (such as a schedule reflecting a patient's circadian rhythm) for switching intensity levels. Some embodiments enable this automatic scheduling only after a minimum amount of time has passed to ensure the consistency of the patient back-out requests. Some embodiments enable the patient or a physician to disable this automatic scheduling feature, accounting for the possibility that the patient may not always trigger the back-out at a consistent time.

Some embodiments allow the patient to trigger the device to temporarily lower or shut off stimulation when desired. For example, some vagal stimulation may alter the voice. These embodiments may be used to allow the patient to stop voice alterations during periods of long conversation. The stimulation may return to the stimulation intensity present at the time of the trigger after a set or physician programmable period of time, or may incrementally step back to the stimulation intensity present at the time of the trigger according to a set of programmable time intervals or schedule.

In some embodiments, the stimulation and control circuit also includes at least one timer or counter, used to determine the neural stimulation dose. The counter can be used to count detected recurring events, such as events in a cardiac cycle or neural stimulation pulses.

The illustrated stimulation control circuit 106 includes a therapy dose controller 111. The illustrated therapy dose controller 620 includes a therapy monitor and a timer, and is configured to determine an amount of the therapy over a defined therapy window, compare the amount of the therapy over the defined therapy window to a defined therapy amount, and change the response to the trigger if the amount of the therapy over the defined therapy window is less than the defined therapy amount. The illustrated override controller 112 includes a trigger counter and a timer, and is configured to count a number of detected triggers over a defined period, compare the the number of detected triggers over the defined period to a defined number of triggers, and automatically interrupt the up-titration routine until an authorized individual resets the therapy when the number of detected triggers over the defined period reaches the defined number of triggers.

Titration, as used herein, refers to the process of adjusting the dose of the stimulation, ultimately to a level that is therapeutically or prophylactically effective. The dose includes an amount or intensity of the neural stimulation, and also includes the number of times the neural stimulation is delivered over a period of time. The intensity of the neural stimulation may be adjusted by adjusting parameters such as amplitude, duty cycle, duration, and or frequency of the neural stimulation, or the number of neural stimulation events that occur over a period of time. FIG. 2 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 213) is delivered, and intervals of stimulation being OFF, when no stimulation pulses are delivered. Thus, for example, some embodiments deliver a plurality of monophasic or biphasic pulses within a neural stimulation burst illustrated in FIG. 2. Pulses delivered within a burst 213 may be delivered at a pulse frequency. These pulses also have an amplitude. Both the pulse frequency and the pulse amplitude affect the dose of the neural stimulation therapy. The duration of the stimulation ON interval is sometimes referred to as the stimulation duration or burst duration. The burst duration also affects the dose of the neural stimulation therapy. The start of a stimulation ON interval is a temporal reference point NS Event. The time interval between successive NS Events is the INS Interval, which is sometimes referred to as the stimulation period or burst period 214. The burst period 214 or the number of neural stimulation events that occur over a time period also affect the dose of the neural stimulation. For an application of neural stimulation to be intermittent, the stimulation duration (i.e., ON interval) is less than the stimulation period (i.e., INS Interval) when the neural stimulation is being applied. The duration of the OFF intervals of INS are determined by the durations of the ON interval and the INS Interval. The duration of the ON interval relative to the INS Interval (e.g., expressed as a ratio) is sometimes referred to as the duty cycle of the INS.

FIG. 3 illustrates a memory, according to various embodiments, that includes instructions 315, operable on by the stimulation control circuitry, for controlling an up-titration routine by progressively stepping up through defined parameter sets (e.g. parameter set 1 through parameter set N), where each set incrementally increases the stimulation dose or intensity of the stimulation therapy. This memory may be illustrated as part of a therapy titration/adjustment module 307. The memory may include a plurality of neural stimulation parameter sets, where each set includes a unique combination of parameter values for the neural stimulation and wherein each unique combination of parameter values is defined to provide neural stimulation therapy at an intensity level. The instructions include instructions for stepping through the plurality of neural stimulation parameter sets according to a schedule to increase the intensity of the therapy until the therapy is at the desired long term intensity. The override controller 112 of FIG. 1 is configured to override the instructions for stepping through the increments of increasing intensity. Various embodiments provide a neural stimulation routine that automatically finds the desirable combination of therapy parameters (e.g. amplitude, pulse width, duty cycle) that provides a desired therapy intensity level.

According to various embodiments, the increment size is programmable, and some of these embodiments limit the increment size to a maximum value. In some embodiments, the increment number is programmable, and some of these embodiments limit the increment number to a maximum number. According to some embodiments, both the increment size and increment number are programmable. In some embodiments, by way of example, a clinician can program both the increment size and the number of increments as long as both the size and number remain with allowed ranges. Some embodiments are programmed with default values for the increment size, some embodiments are programmed with default values for the increment number, and some embodiments are programmed with default values for both the increment size and increment number.

The system is configured to increment the dose or intensity of the neural stimulation according to a programmed schedule or time table. By way of example and not limitation, the programmed schedule may increment the dose on an hourly, daily, weekly, or monthly basis. Other time increments may be used. The time increments may be the same increments, or may be different increments. For example, some embodiments are configured to allow the physician to program the system to increment the neural stimulation dose at specific times on specific days. Some system embodiments are programmed with default increment times for incrementing the neural stimulation dose.

Some system embodiments are configured to allow the dose to increment only when specified conditions are met. For example, an activity sensor may be used to detect periods of rest or periods of activity, and the device may be programmed to enable increments only during periods of rest or to enable increments only during periods of activity. Additional conditions may be required as well, such as a time of day, or particular levels for cardiac demand, respiration activity, blood pressure, heart rate, and the like.

FIG. 4 illustrates an embodiment of a therapy titration module 407 such as is illustrated at 107 in FIG. 1. According to various embodiments, the stimulation control circuit is adapted to set or adjust any one or any combination of stimulation features 416. Examples of stimulation features include the amplitude, frequency, polarity and wave morphology of the stimulation signal. Examples of wave morphology include a square wave, triangle wave, sinusoidal wave, and waves with desired harmonic components to mimic naturally-occurring baroreflex stimulation. Some embodiments of the stimulation output circuit are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The therapy titration module 407 can be programmed to change stimulation sites 417, such as changing the stimulation electrodes used for a neural target or changing the neural targets for the neural stimulation. For example, different electrodes of a multi-electrode cuff can be used to stimulate a neural target. Examples of neural targets include the right and left vagus nerves, cardiac branches of the vagus nerve, cardiac fats pads, baroreceptors, the carotid sinus, the carotid sinus nerve, and the aortic nerve. Autonomic neural targets can include afferent pathways and efferent pathways and can include sympathetic and parasympathetic nerves. The stimulation can include stimulation to stimulate neural traffic or stimulation to inhibit neural traffic. Thus, stimulation to evoke a sympathetic response can involve sympathetic stimulation and/or parasympathetic inhibition; and stimulation to evoke a parasympathetic response can involve parasympathetic stimulation and/or sympathetic inhibition.

The therapy titration module 407 can be programmed to change stimulation vectors 418. Vectors can include stimulation vectors between electrodes, or stimulation vectors for transducers. For example, the stimulation vector between two electrodes can be reversed. One potential application for reversing stimulation vectors includes changing from stimulating neural activity at the neural target to inhibiting neural activity at the neural target. More complicated combinations of electrodes can be used to provide more potential stimulation vectors between or among electrodes. One potential stimulation vector application involves selective neural stimulation (e.g. selective stimulation of the vagus nerve) or changing between a selective stimulation and a more general stimulation of a nerve trunk.

The therapy titration module 407 can be programmed to control the neural stimulation according to stimulation instructions, such as a stimulation routine or schedule 419, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit can be programmable. The controller may also terminate a neural stimulation session in response to an interrupt signal, such as may be generated by one or more sensed parameters or any other condition where it is determined to be desirable to stop neural stimulation.

A device may include a programmed therapy schedule or routine stored in memory and may further include a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

According to various embodiments, the stimulation schedule refers to the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2 AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, low heart rate levels, and the like. For example, the stimulation can be synchronized to the cardiac cycle based on detected events that enable the stimulation. The therapy schedule can also specify how the stimulation is delivered.

Some embodiments are configured to change a ramp-up time for increasing one or more stimulation parameters from OFF to a programmed intensity at the start of the ON portion. Patients may tolerate higher stimulation levels if there is not an abrupt change at the start of the duty cycle. The parameter increased during this ramp-up time may be amplitude, for example, or other parameter or other combination of parameters that affect the intensity of the stimulation.

Figure 5:
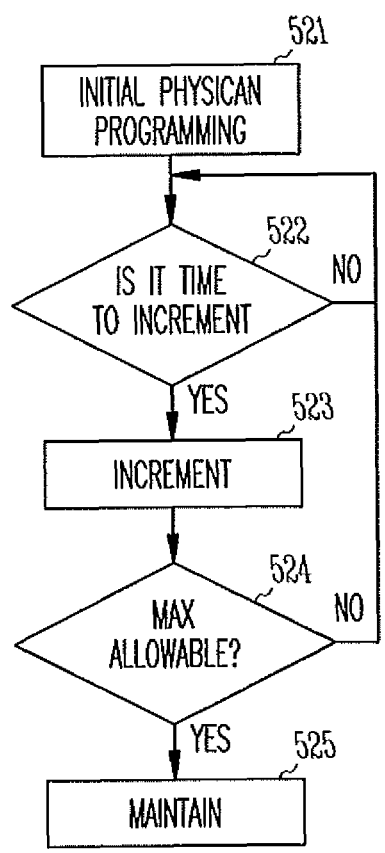
FIG. 5 illustrates an embodiment of a method for implementing an automatic up-titration routine in an implantable medical device.

FIG. 5 illustrates an embodiment of a method for implementing an automatic up-titration routine in an implantable medical device. At 521, the device is programmed by the physician with initial values for the up-titration routine. These programmed values may include the schedule for incrementing the dose, and the dose interval size for increasing the stimulation intensity. At 522, the programmed routine determines if it is time to increment the dose. For example, a clock or timer may be used to determine a time, or an elapsed time from a start point, and the routine may trigger the increment when the time corresponds to a time in the programmed schedule. If the programmed routine determines that it is time to increment the dose, the routine increments the dose at 523. The incrementing process continues until the desired dose is being delivered. For example, the programmed routine may be programmed with a maximum number of allowable increments. If, at 524, the maximum number of allowable increments has not been reached, the process returns to 522 to determine if it is time to perform another increment. If the maximum number of allowable increments has been reached, the process proceeds to 525 to maintain the dose at the desired dose.

Figure 6:
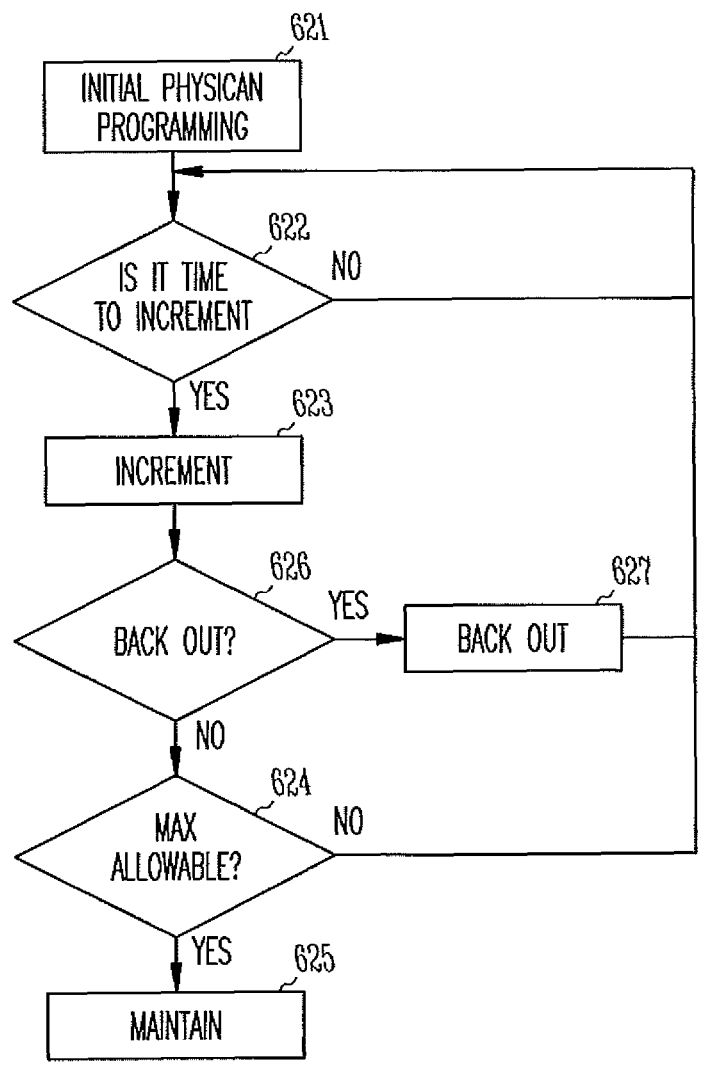
FIG. 6 illustrates an embodiment of a method for implementing an automatic up-titration routine with patient back-out in an implantable medical device.

FIG. 6 illustrates an embodiment of a method for implementing an automatic up-titration routine with patient backout in an implantable medical device. At 621, the device is programmed by the physician with initial values for the up-titration routine. These programmed values may include the schedule for incrementing the dose, and the dose interval size for increasing the stimulation intensity. At 622, the programmed routine determines if it is time to increment the dose. For example, a clock or timer may be used to determine a time, or an elapsed time from a start point, and the routine may trigger the increment when the time corresponds to a time in the programmed schedule. If the programmed routine determines that it is time to increment the dose, the routine increments the dose at 623, and then determines at 626 if the patient is requesting a back-out of the last increment that was performed at 623. If the patient is requesting a back-out, then the process proceeds to 627 to back out or reduce the dose by a level, and then returns to 622 to determine if it is time to increment a dose. The incrementing process continues until the desired dose is being delivered. For example, the programmed routine may be programmed with a maximum number of allowable increments. If the patient is not requesting a back-out at 626, the process proceeds to 624 to determine if it the maximum number of allowable increments has been reached. If, at 624, the maximum number of allowable increments has not been reached, the process returns to 622 to determine if it is time to increment a dose. If the maximum number of allowable increments has been reached, then the process proceeds to 625 to maintain the dose at the desired dose.

Figure 7:
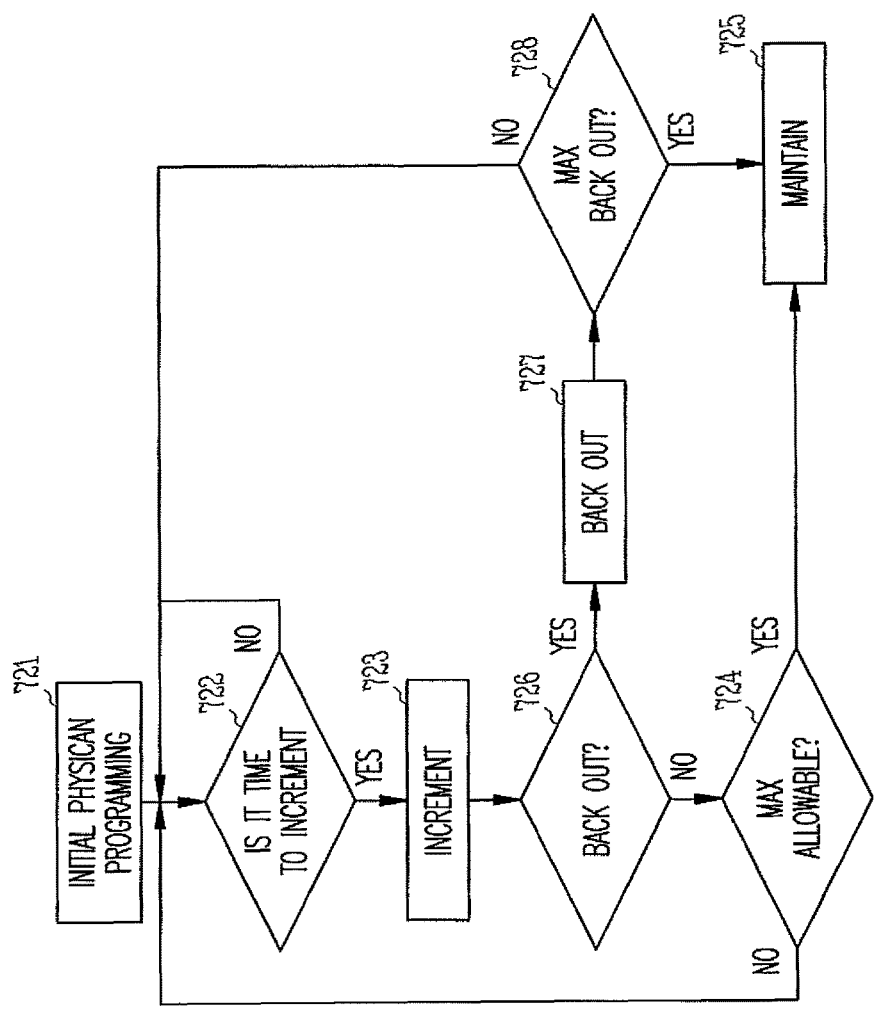
FIG. 7 illustrates an embodiment of a method for implementing an automatic up-titration routine in an implantable medical device, wherein the routine limits the number of patient back-outs that will be performed.

FIG. 7 illustrates an embodiment of a method for implementing an automatic up-titration routine in an implantable medical device, wherein the routine limits the number of patient back-outs that will be performed. At 721, the device is programmed by the physician with initial values for the up-titration routine. These programmed values may include the schedule for incrementing the dose, and the dose interval size for increasing the stimulation intensity. At 722, the programmed routine determines if it is time to increment the dose. For example, a clock or timer may be used to determine a time, or an elapsed time from a start point, and the routine may trigger the increment when the time corresponds to a time in the programmed schedule. If the programmed routine determines that it is time to increment the dose, the routine increments the dose at 723, and then determines at 726 if the patient is requesting a back-out of the last increment that was performed at 723. If the patient is requesting a back-out, then the process proceeds to 727 to back out or reduce the dose by a level, and then proceeds to 728 to determine if the maximum number of allowable back-outs has already been performed. If the back-out at 727 was the last allowable back-out, as determined by a programmed limit in the device, then the process proceeds to 725 to maintain the dose at this reduced level. If the patient is not requesting a back-out, the process proceeds to 724 to determine if the maximum number of allowable increments has been reached. The incrementing process continues until the desired dose is being delivered. For example, the programmed routine may be programmed with a maximum number of allowable increments. If, at 724, the maximum number of allowable increments has been reached, the process proceeds to 725 to maintain the dose at the desired dose. If the maximum number of allowable increments has not been reached, the process returns to 722 to determine if it is time to increment.

Figure 8:
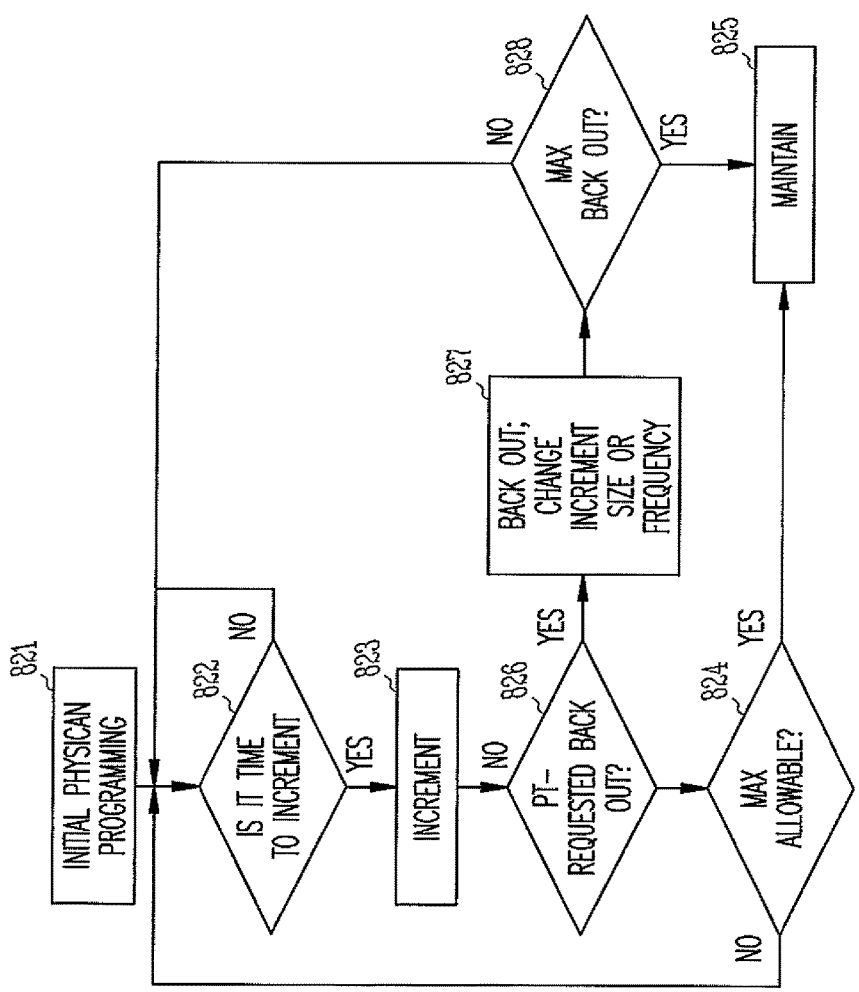
FIG. 8 illustrates an embodiment of a method for implementing an automatic up-titration routine in an implantable medical device, wherein the routine changes the increment size or increment frequency in response to a patient back-out.

FIG. 8 illustrates an embodiment of a method for implementing an automatic up-titration routine in an implantable medical device, wherein the routine changes the increment size or increment frequency in response to a patient back-out. At 821, the device is programmed by the physician with initial values for the up-titration routine. These programmed values may include the schedule for incrementing the dose, and the dose interval size for increasing the stimulation intensity. At 822, the programmed routine determines if it is time to increment the dose. For example, a clock or timer may be used to determine a time, or an elapsed time from a start point, and the routine may trigger the increment when the time corresponds to a time in the programmed schedule. If the programmed routine determines that it is time to increment the dose, the routine increments the dose at 823 and proceeds to 826 where it is determined if the patient is requesting a back-out of the last increment that was performed at 823.

If the patient is not requesting a back-out, the process returns to 822 to determine if it is time to perform another increment. If the patient is requesting a back-out, then the process proceeds to 827 to back out or reduce the dose by a level and also to change the size or frequency of the increments, and then proceeds to 828 to determine if the maximum number of allowable back-outs has already been performed. If the back-out at 827 was the last allowable back-out, as determined by a programmed limit in the device, then the process proceeds to 825 to maintain the dose at this reduced level. The incrementing process continues until the desired dose is being delivered. For example, the programmed routine may be programmed with a maximum number of allowable increments. If, at 824, the maximum number of allowable increments has not been reached, the process returns to 822 to determine if it is time to increment the dose. If at 824, it is determined that the maximum number of allowable increments has been performed, the process proceeds to 825 to maintain the dose at the desired dose.

Figure 9:
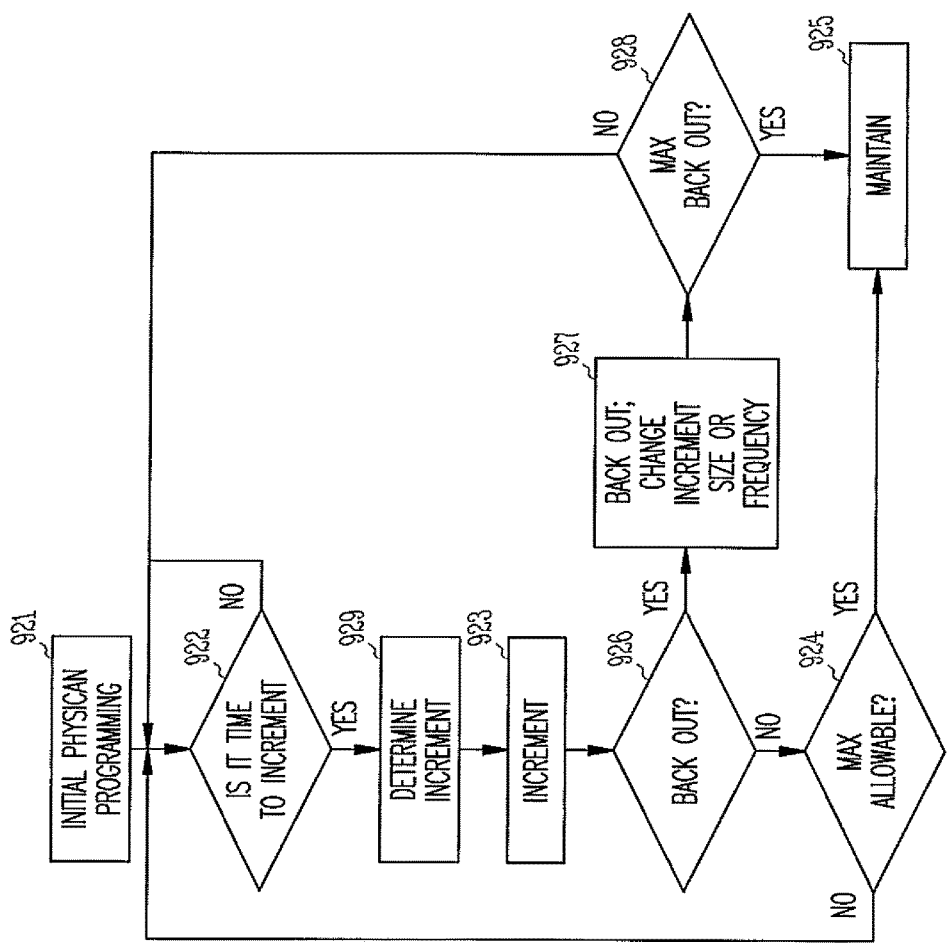
FIG. 9 illustrates an embodiment of a method for implementing an automatic up-titration routine in an implantable medical device, wherein the routine determines the dose increment based on current setting and/or number of times backed out and/or other determinants.

FIG. 9 illustrates an embodiment of a method for implementing an automatic up-titration routine in an implantable medical device, wherein the routine determines the dose increment based on current setting and/or number of times backed out and/or other determinants. The increment frequency may be used as a surrogate for the number of times that the up-titration routine was backed out. At 921, the device is programmed by the physician with initial values for the up-titration routine. These programmed values may include the schedule for incrementing the dose, and the dose interval size for increasing the stimulation intensity. At 922, the programmed routine determines if it is time to increment the dose. For example, a clock or timer may be used to determine a time, or an elapsed time from a start point, and the routine may trigger the increment when the time corresponds to a time in the programmed schedule. If the programmed routine determines that it is time to increment the dose, the routine determines the increment at 929 and then at 923 increments the dose as determined at 929. The increment may be based on a current setting of the neural stimulation, based on the number of times that the patient requests a back-out, based on other determinants such as sensed physiological responses to the stimulation, patient activity, and/or tune, or based on various combinations of these factors. At 926, it is determined whether the patient is requesting a back-out. If the patient is requesting a back-out, then the process proceeds to 927 to back out or reduce the dose by a level and also to change the size or frequency of the increments, and then proceeds to 928 to determine if the maximum number of allowable back-outs has already been performed. If the back-out at 927 was the last allowable back-out, as determined by a programmed limit in the device, then the process proceeds to 925 to maintain the dose at this reduced level. The incrementing process continues until the desired dose is being delivered. For example, the programmed routine may be programmed with a maximum number of allowable increments. If the patient is not requesting a back-out, the process returns to 924 to determine if the maximum number allowable increments have been performed. If the maximum number of allowable back-outs has not been reached, then the process returns to 922 to determine if it is time to increment the dose. If at 924, it is determined that the maximum number of allowable increments has been performed, the process proceeds to 925 to maintain the dose at the desired dose.

Those of ordinary skill in the art will appreciate, upon reading and comprehending this document, that the routines illustrated in FIGS. 6-9 are examples. The present subject matter is not intended to be limited to routines with specific sequences. By way of example, the back-out can be delivered by the patient, and sensed and responded to by the device at any tune. For example, the device need not be programmed to act in a step-wise manner of linearly moving from one action to the next. Some device embodiments sit in a "wait-loop" state where the device waits for either the next time to up-increment the dose or a patient-requested back-out occurs. The device performs the up-increment or patient-requested back-out, and then waits again for either the next up-increment time or the next patient-requested back-out.

Figure 10:
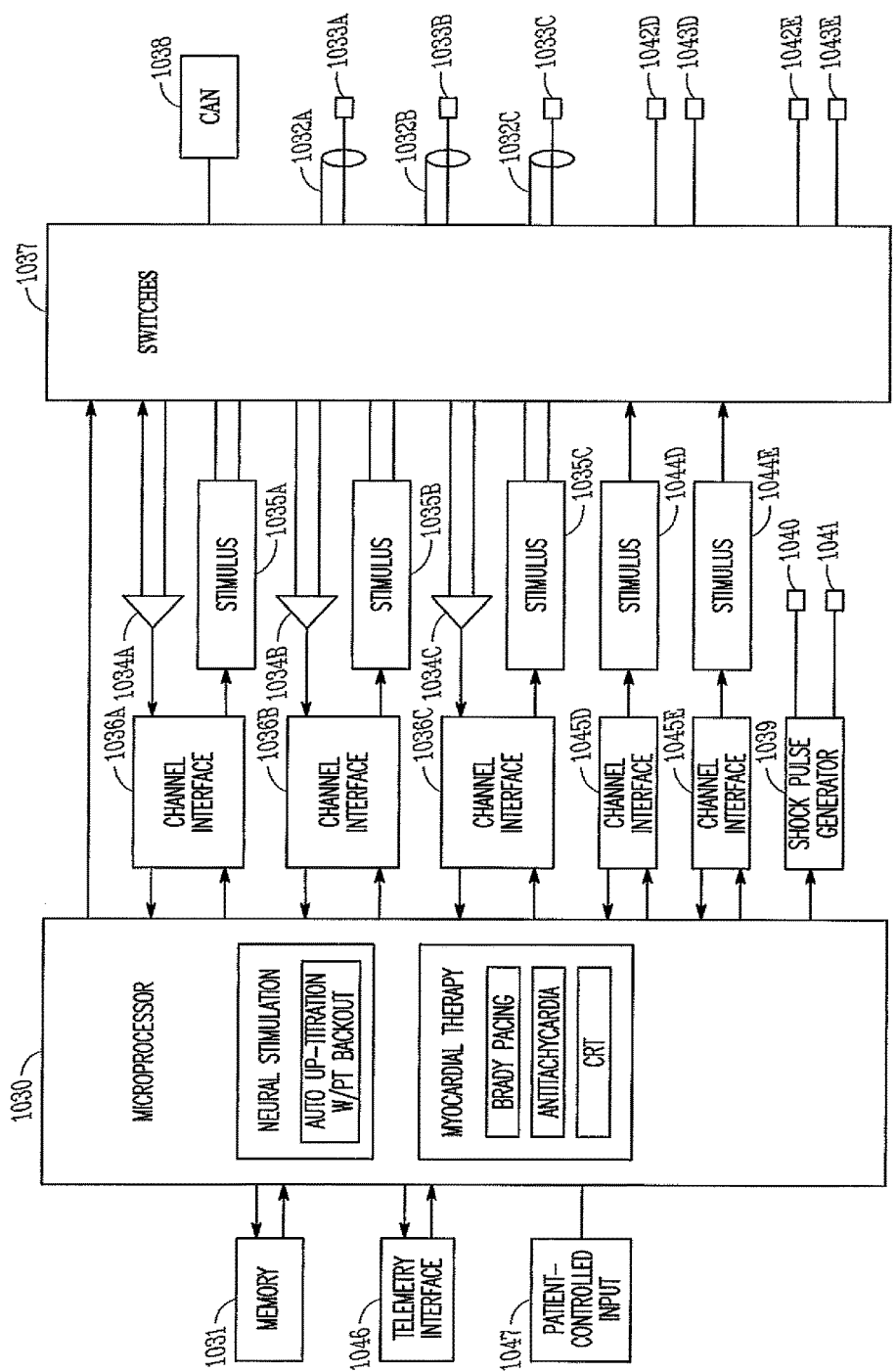
FIG. 10 shows a system diagram of an embodiment of a microprocessor-based implantable device, according to various embodiments.

FIG. 10 shows a system diagram of an embodiment of a microprocessor-based implantable device, according to various embodiments. The controller of the device is a microprocessor 1030 which communicates with a memory 1031 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1032A-C and tip electrodes 1033A-C, sensing amplifiers 1034A-C, pulse generators 1035A-C, and channel interfaces 1036A-C. Each chaimel thus includes a pacing channel made up of the pulse generator connected to the electrode and a sensing channel made up of the sense amplifier connected to the electrode. The channel interfaces communicate bidirectionally with the microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias. The sensing of these channels can be used to detect cardiac activity for use in synchronizing neural stimulation and for use as feedback in titrating the neural stimulation.

The electrodes of each bipolar lead are connected via conductors within the lead to a switching network 1037 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1038 or an electrode on another lead serving as a ground electrode. A shock pulse generator 1039 is also interfaced to the controller for delivering a defibrillation shock via a pair of shock electrodes 1040 and 1041 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1042 and a second electrode 1043D, a pulse generator 1044D, and a channel interface 1045D, and the other charnel includes a bipolar lead with a first electrode 1042E and a second electrode 1043E, a pulse generator 1044E, and a channel interface 1045E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1046 connected to the microprocessor, which can be used to communicate with an external device. Also illustrated is a patient-controlled input 1047 to the microprocessor 1030. The therapy routines performed by the microprocessor are configured to respond to the patient-controlled input by, for example, backing out of the last increment implemented by the automatic up-titration routine. The illustrated microprocessor is capable of performing neural stimulation therapy routines and myocardial (CRM) stimulation routines. The neural stimulation routines can target nerves to affect cardiac activity (e.g. heart rate and contractility). The neural stimulation routines can include programmed routines for responding to patient-controlled indicators, as disclosed in various embodiments in this document. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 11:
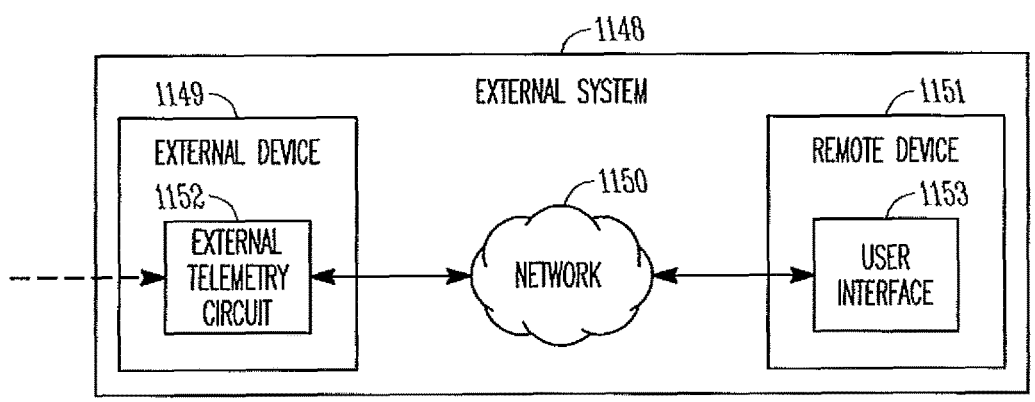
FIG. 11 is a block diagram illustrating an embodiment of an external system.

FIG. 11 is a block diagram illustrating an embodiment of an external system 1148. The external system includes a programmer, in some embodiments. In the illustrated embodiment, the external system includes a patient management system. As illustrated, the external system 1148 is a patient management system including an external device 1149, a telecommunication network 1150, and a remote device 1151. The external device 1149 is placed within the vicinity of an IMD and includes external telemetry system 1152 to communicate with the IMD. Remote device(s) 1151 is in one or more remote locations and communicates with external device 1149 through network 1150, thus allowing a physician or other caregiver to monitor and treat a patient from a distant location and/or allowing access to various treatment resources from the one or more remote locations. The illustrated remote device includes a user interface 1153.

Figure 12:
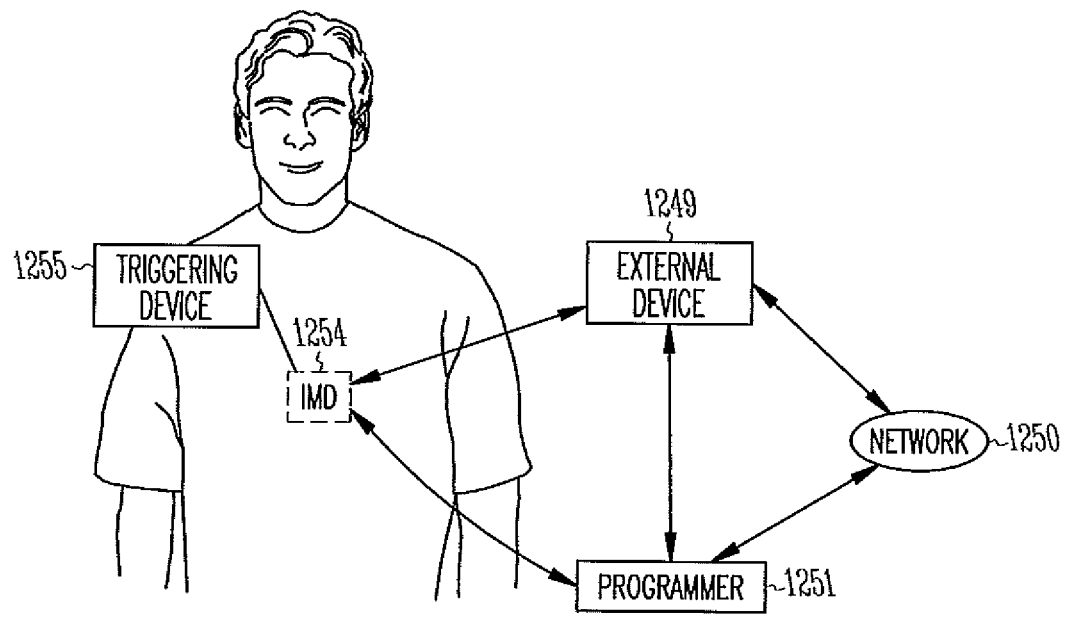
FIGS. 12 and 13 illustrate embodiments of a system that includes an implantable medical device and an external system.
Figure 13:
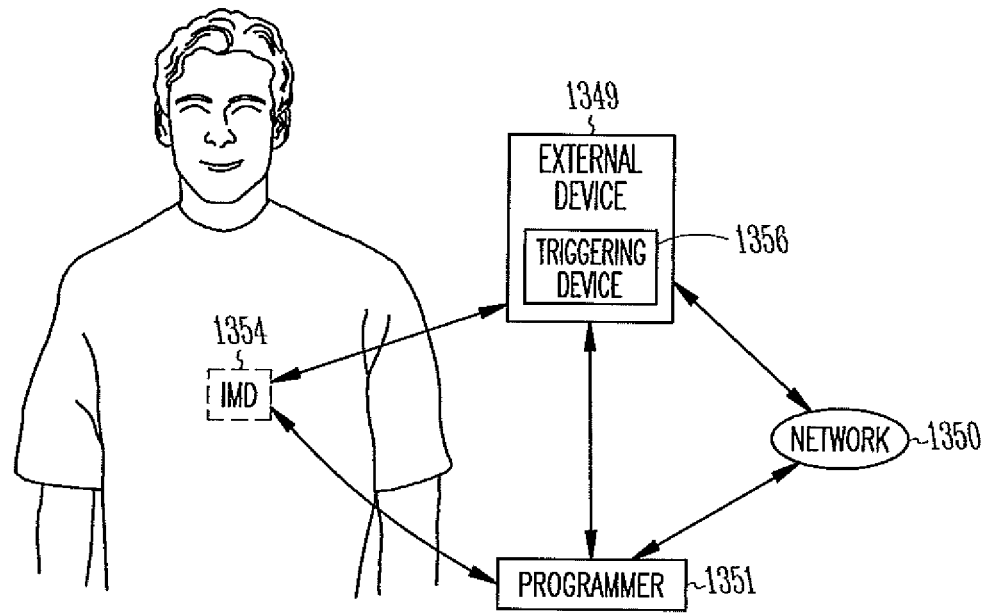

FIGS. 12 and 13 illustrate embodiments of a system that includes an IMD an external system. FIG. 12 illustrates a system with an IMD 1254, a patient-operated external device 1249, a programmer 1251 that may be in a clinical setting, a network 1250 for communication between the external device 1249 and the programmner 1251, and a patient-operated triggering device 1255 for use by the patient to request back-outs. In some embodiments, the programmer and external device are capable of direct communications in place of or in addition to the network communication. The external device is capable of communicating with the IMD. The illustrated triggering device can be a variety of device configured to communicate a variety of triggering signals to the IMD 1254. For example, various embodiments of a triggering device 1255 are configured to communicate a triggering signal to the IMD 1254 using electrical pulses, mechanical or vibrational signals, sound and/or light. An electrical signal could be delivered at very low amplitudes, and a fixed frequency. A sound-based triggering device may emit sound using a piezo element, and the light-based triggering device may emit light via a light emitting diode (LED). Various embodiments of the IMD use electrodes to sense the electrical signal, piezo sensor or other pressure sensor to sense the mechanical or vibrations, or optical sensors to sense light. In various embodiments, the triggering device is designed as an inexpensive package that can be easily carried by the patient. For example, some embodiments are designed to be carried similar to a key fob. In various embodiments, the trigger device 1255 and IMD 1254 are configured to allow the IMD 1254 to receive a trigger signal when the triggering device is held against or near the patient's body near the IMD 1254. In some embodiments, the patient actuates a button or other actuator to send the trigger signal. FIG. 13 illustrates a system with an IMD 1354, a patient-operated external device 1349, a programmer 1351 that may be in a clinical setting, a network 1350 for communication between the external device 1349 and the programmer 1351. In the system illustrated in FIG. 13, the patient-operated external device 1349 includes or functions as a patient-operated triggering device 1356 for use by the patient to request back-outs. For example, the external device 1349 communicates with the IMD 1354. These devices 1349 and 1354 can be configured to communicate patient-requested back-out triggers fro the external device 1349 to the IMD 1354.

Some system embodiments are configured to allow the patient or physician to go back and retrieve information regarding the triggers that alter therapy. For example, if numerous triggers by the patient interrupt therapy, some embodiments run a report on the overall trigger use. This information can be used to verify that the system is working appropriately.

As will be understood by one of ordinary skill in the art upon reading and comprehending the present subject matter, various embodiments of the present subject matter improve patient acceptance of therapy, maintain efficacious levels of therapy, allow patient flexibility in therapy management, and generally improve the quality of life of the patient who is receiving the NCT. The modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable neural stimulator for implantation in a patient, comprising:

controller circuitry;
neural stimulation output circuitry configured to deliver neural stimulation, wherein the controller circuitry is configured to control an intensity of the neural stimulation delivered by the neural stimulation output circuitry;
an input configured to receive a patient-controlled trigger, wherein the controller circuitry is configured to detect the patient-controlled trigger;
a memory with instructions operable on by the controller circuitry, wherein the instructions include:
  instructions for delivering neural stimulation using the neural stimulation output circuitry;
  instructions for implementing an up-titration routine to automatically increase the intensity of the neural stimulation from a lower intensity level to a higher intensity level; and
  instructions for automatically decreasing the intensity of the neural stimulation from the higher intensity level to the lower intensity level in response to receiving the patient-controlled trigger, wherein the automatically increased intensity is maintained if the trigger from the patient is not received,
wherein the neural stimulator is configured to detect a specific condition, and the neural stimulator is configured to allow the up-titration routine, implemented by the controller circuitry operating on the instructions in the memory, to increase the intensity only when the specific condition is detected.

2. The stimulator of claim 1, wherein the memory includes a plurality of neural stimulation parameter sets, each of the neural stimulation parameter sets correspond to one of a plurality of intensity levels for the neural stimulation, and the instructions for implementing the up-titration routine includes instructions for progressively increasing the intensity using the plurality of parameter sets.

3. The stimulator of claim 2, wherein the plurality of neural stimulation parameter sets include different values for at least one parameter selected from the group of parameters consisting of: an amplitude of the neural stimulation, a duration of the neural stimulation, a pulse width of the neural stimulation, a duty cycle of neural stimulation, a burst frequency of the neural stimulation, a programmed schedule for the neural stimulation, a vector of the neural stimulation, and a ramp-up time from OFF to a programmed intensity at the start of the ON portion.

4. The stimulator of claim 1, wherein the instructions for implementing an up-titration routine include a physician-programmable intensity interval.

5. The stimulator of claim 1, wherein the instructions for implementing an up-titration routine include a physician-programmable time for incrementing the intensity.

6. The stimulator of claim 1, wherein the instructions for implementing an up-titration routine include:
instructions for determining if it is time to increment the intensity of the neural stimulation, and incrementing the intensity of the neural stimulation when it is time to increment; and
instructions for maintaining the intensity of the neural stimulation if the intensity level has been increased to a maximum allowable level.

7. The stimulator of claim 6, wherein the instructions for automatically decreasing the intensity of the neural stimulation from the higher intensity level to the lower intensity level in response to receiving the patient-controlled trigger includes instructions for determining if there has been a maximum number of allowable back-outs and maintaining a current intensity level if there has been the maximum number of allowable back-outs.

8. The stimulator of claim 6, wherein the instructions for automatically decreasing the intensity of the neural stimulation from the higher intensity level to the lower intensity level in response to receiving the patient-controlled trigger includes instructions for changing an increment size between successive intensity levels.

9. The stimulator of claim 6, wherein the instructions for automatically decreasing the intensity of the neural stimulation from the higher intensity level to the lower intensity level in response to receiving the patient-controlled trigger includes instructions for changing an increment time between successive intensity levels.

10. The stimulator of claim 6, wherein the instructions for implementing an up-titration routine further include instructions for determining an incremental change in the intensity for use in incrementing the intensity of the neural stimulation when it is time to increment.

11. The stimulator of claim 1, wherein the instructions for automatically decreasing the intensity of the neural stimulation from the higher intensity level to the lower intensity level in response to receiving the patient-controlled trigger include instructions for automatically reversing at least one additional intensity increase in response to receiving an additional patient-controlled trigger.

12. The stimulator of claim 1, further comprising an activity detector configured to detect the specific condition.

13. The stimulator of claim 12, wherein the activity detector is configured to detect a period of rest, the specific condition being the period of rest.

14. The stimulator of claim 12, wherein the activity detector is configured to detect a period of activity, the specific condition being the period of activity.

15. An implantable neural stimulator for implantation in a patient, comprising:
controller circuitry;
neural stimulation output circuitry configured to deliver neural stimulation, wherein the controller circuitry is configured to control an intensity of the neural stimulation delivered by the neural stimulation output circuitry;
an input configured to receive a patient-controlled trigger, wherein the controller circuitry is configured to detect the patient-controlled trigger;
a memory with instructions operable on by the controller circuitry, wherein the instructions include:
instructions for delivering neural stimulation using the neural stimulation output circuitry;
instructions for implementing an up-titration routine to automatically increase the intensity of the neural stimulation from a lower intensity level to a higher intensity level; and
instructions for automatically decreasing the intensity of the neural stimulation from the higher intensity level to the lower intensity level in response to receiving the patient-controlled trigger, wherein the automatically increased intensity is maintained if the trigger from the patient is not received;
an activity detector configured to detect a specific condition, the specific condition being a period of rest or a period of activity,
wherein the neural stimulator is configured to use detection of the specific condition to enable the automatic increase in the intensity by the up-titration routine.

* * * * *